(12) United States Patent
Johnson et al.

(10) Patent No.: US 10,874,841 B2
(45) Date of Patent: *Dec. 29, 2020

(54) BIOPSY SITE MARKER APPLIER

(71) Applicant: Devicor Medical Products, Inc., Cincinnati, OH (US)

(72) Inventors: Michael E. Johnson, West Chester, OH (US); Timothy Zimmer, Centerville, OH (US); Alberto Cambero Rangel, Empalme (MX)

(73) Assignee: Devicor Medical Products, Inc., Cincinnati, OH (US)

( * ) Notice: Subject to any disclaimer, the term of this patent is extended or adjusted under 35 U.S.C. 154(b) by 604 days.

This patent is subject to a terminal disclaimer.

(21) Appl. No.: 14/205,851

(22) Filed: Mar. 12, 2014

(65) Prior Publication Data

US 2014/0276037 A1  Sep. 18, 2014

Related U.S. Application Data

(60) Provisional application No. 61/787,555, filed on Mar. 15, 2013, provisional application No. 61/812,275, filed on Apr. 16, 2013.

(51) Int. Cl.
*A61M 37/00* (2006.01)
*A61B 10/02* (2006.01)
(Continued)

(52) U.S. Cl.
CPC ..... *A61M 37/0069* (2013.01); *A61B 10/0266* (2013.01); *A61B 90/39* (2016.02); *A61B 17/3468* (2013.01); *A61B 2090/3987* (2016.02)

(58) Field of Classification Search
CPC ............... A61M 37/0069; A61B 90/39; A61B 10/0266; A61B 2090/3987; A61B 17/3468
See application file for complete search history.

(56) References Cited

U.S. PATENT DOCUMENTS 2,972,779 A * 2/1961 Cowley ............. A61M 25/0015
216/53
5,034,005 A   7/1991 Appling
(Continued)

FOREIGN PATENT DOCUMENTS

CN   1082125 A   7/2006
CN   101518466 A   9/2009
(Continued)

OTHER PUBLICATIONS

U.S. Appl. No. 61/787,555, filed Mar. 15, 2013.
(Continued)

*Primary Examiner* — James M Kish

(74) *Attorney, Agent, or Firm* — Frost Brown Todd LLC

(57) ABSTRACT

A marker delivery device comprises a marker deployer cannula, a push rod, a biopsy site marker, and a ramped tip. The marker deployer cannula may have a marker exit in communication with an interior lumen of the cannula. The marker exit may comprise a distal end with a ramped surface. The biopsy site marker may be configured with a plurality of edges. The plurality of edges may be configured to engage at least a portion of the interior lumen of the cannula. The ramped tip may comprise a first ramped surface and a second ramped surface, the second ramped surface may align with the ramped surface of the distal end of the marker exit. The push rod may be used to push the biopsy site marker up the ramped tip and through the marker exit.

17 Claims, 12 Drawing Sheets

(51) Int. Cl.
*A61B 90/00* (2016.01)
*A61B 17/34* (2006.01)

(56) References Cited

U.S. PATENT DOCUMENTS

| | | | |
|---|---|---|---|
| 5,526,822 A | 6/1996 | Burbank et al. | |
| 5,928,164 A | 7/1999 | Burbank et al. | |
| 6,017,316 A | 1/2000 | Ritchart et al. | |
| 6,086,544 A | 7/2000 | Hibner et al. | |
| 6,162,187 A | 12/2000 | Buzzard et al. | |
| 6,228,055 B1 | 5/2001 | Foerster et al. | |
| 6,347,241 B2* | 2/2002 | Burbank | A61K 49/006 378/62 |
| 6,356,782 B1* | 3/2002 | Sirimanne | A61K 49/006 600/431 |
| 6,371,904 B1 | 4/2002 | Sirimanne et al. | |
| 6,432,065 B1 | 8/2002 | Burdorff et al. | |
| 6,626,849 B2 | 9/2003 | Huitema et al. | |
| 6,752,768 B2 | 6/2004 | Burdorff et al. | |
| 6,993,375 B2 | 1/2006 | Burbank et al. | |
| 6,996,433 B2 | 2/2006 | Burbank et al. | |
| 7,044,957 B2 | 5/2006 | Foerster et al. | |
| 7,047,063 B2 | 5/2006 | Burbank et al. | |
| 7,229,417 B2 | 6/2007 | Foerster et al. | |
| 7,442,171 B2 | 10/2008 | Stephens et al. | |
| 7,465,279 B2 | 12/2008 | Beckman et al. | |
| 7,648,466 B2 | 1/2010 | Stephens et al. | |
| 7,837,632 B2 | 11/2010 | Stephens et al. | |
| 7,854,706 B2 | 12/2010 | Hibner | |
| 7,914,464 B2 | 3/2011 | Burdorff et al. | |
| 7,938,786 B2 | 5/2011 | Ritchie et al. | |
| 8,083,687 B2 | 12/2011 | Parihar | |
| 8,118,755 B2 | 2/2012 | Hibner et al. | |
| 8,206,316 B2 | 6/2012 | Hibner et al. | |
| 8,241,226 B2 | 8/2012 | Hibner et al. | |
| 8,251,916 B2 | 8/2012 | Speeg et al. | |
| 8,454,531 B2 | 6/2013 | Speeg et al. | |
| 8,532,747 B2 | 9/2013 | Nock et al. | |
| 8,622,924 B2 | 1/2014 | Speeg et al. | |
| 8,702,623 B2 | 4/2014 | Parihar et al. | |
| 8,764,680 B2 | 7/2014 | Rhad et al. | |
| 8,801,742 B2 | 8/2014 | Rhad et al. | |
| 8,858,465 B2 | 10/2014 | Fiebig | |
| 8,938,285 B2 | 1/2015 | Fiebig et al. | |
| 9,326,755 B2 | 5/2016 | Fiebig et al. | |
| 9,345,457 B2 | 5/2016 | Speeg et al. | |
| 9,414,816 B2 | 8/2016 | Rhad et al. | |
| 2006/0074345 A1 | 4/2006 | Hibner | |
| 2006/0122503 A1 | 6/2006 | Burbank et al. | |
| 2006/0235298 A1* | 10/2006 | Kotmel | A61B 1/018 600/431 |
| 2008/0086142 A1* | 4/2008 | Kohm | A61B 17/3472 606/92 |
| 2008/0146962 A1 | 6/2008 | Ritchie et al. | |
| 2009/0131821 A1 | 5/2009 | Speeg et al. | |
| 2009/0216115 A1* | 8/2009 | Seiler | A61B 90/98 600/426 |
| 2010/0049084 A1* | 2/2010 | Nock | A61B 90/39 600/562 |
| 2010/0049085 A1 | 2/2010 | Nock et al. | |
| 2010/0152610 A1 | 6/2010 | Parihar et al. | |
| 2010/0160819 A1 | 6/2010 | Parihar et al. | |
| 2010/0198140 A1* | 8/2010 | Lawson | A61B 17/7095 604/57 |
| 2010/0222672 A1 | 9/2010 | Macfarlane et al. | |
| 2010/0234726 A1* | 9/2010 | Sirimanne | A61K 49/006 600/426 |
| 2011/0071391 A1* | 3/2011 | Speeg | A61M 5/427 600/431 |
| 2011/0098595 A1* | 4/2011 | Hibner | A61B 17/3468 600/562 |
| 2012/0330186 A1* | 12/2012 | Rhad | A61B 10/0275 600/567 |
| 2013/0324882 A1 | 12/2013 | Mescher | |

FOREIGN PATENT DOCUMENTS

| | | |
|---|---|---|
| CN | 101653382 A | 2/2010 |
| JP | 2003-503098 A | 1/2003 |
| JP | 2005-288175 A | 10/2005 |
| JP | 2006-528907 A | 12/2006 |
| JP | 2009-509709 A | 3/2009 |
| JP | 2010-046483 A | 3/2010 |
| WO | WO 2012/154988 A2 | 11/2012 |

OTHER PUBLICATIONS

U.S. Appl. No. 61/812,275, filed Apr. 16, 2013.
European Search Report of related European Patent Application No. 14768898.0 dated Sep. 22, 2016. 6 Total Pages.
Extended European Search Report of related European Patent Application No. 14768898.0 dated Feb. 1, 2017.
Chinese Office Action, First Office Action, and Search Report dated May 2, 2017 for Application No. CN 201480016115.8, 12 pgs.
International Search Report and Written Opinion dated Sep. 12, 2014 for Application No. PCT/US2014/024452, 14 pgs.
European Intention to Grant dated Jul. 13, 2018 for Application No. EP 14768898.0, 38 pgs.
Chinese Office Action, Second Office Action, dated Jan. 2, 2018 for Application No. CN 201480016115.8, 10 pgs.
Chinese Office Action, Decision of Rejection, dated Apr. 24, 2018 for Application No. CN 201480016115.8, 8 pgs.
Chinese Office Action, Notification of Acceptance of Request for Reexamination, dated Jul. 18, 2018 for Application No. CN 201480016115.8, 2 pgs.
Japanese Office Action, Notice of Reasons for Refusal, dated Oct. 11, 2017 for Application No. JP 2016-501540, 4 pgs.
Japanese Office Action, Notification of Allowance, dated Jul. 10, 2018 for Application No. JP 2016-501540, 3 pgs.
U.S. Appl. No. 61/566,793, filed Dec. 5, 2011.

* cited by examiner

BIOPSY SITE MARKER APPLIER

PRIORITY

This application claims priority to U.S. Provisional Patent App. No. 61/812,275, entitled "Biopsy Site Marker Applier," filed Apr. 16, 2013, the disclosure of which is incorporated by reference herein. Additionally, this application claims priority to U.S. Provisional Patent App. No. 61/787,555, entitled "Biopsy Site Marker Applier with Compound Ramp," filed Mar. 15, 2013, the disclosure of which is incorporated by reference herein.

BACKGROUND

Biopsy samples have been obtained in a variety of ways in various medical procedures using a variety of devices. Biopsy devices may be used under stereotactic guidance, ultrasound guidance, MRI guidance, PEM guidance, BSGI guidance, or otherwise.

Merely exemplary biopsy devices are disclosed in U.S. Pat. No. 5,526,822, entitled "Method and Apparatus for Automated Biopsy and Collection of Soft Tissue," issued Jun. 18, 1996; U.S. Pat. No. 6,086,544, entitled "Control Apparatus for an Automated Surgical Biopsy Device," issued Jul. 11, 2000; U.S. Pub. No. 2003/0109803, entitled "MRI Compatible Surgical Biopsy Device," published Jun. 12, 2003, patented as U.S. Pat. No. 6,626,849; U.S. Pub. No. 2007/0118048, entitled "Remote Thumbwheel for a Surgical Biopsy Device," published May 24, 2007, patented as U.S. Pat. No. 7,442,171; U.S. Pat. No. 7,938,786, entitled "Vacuum Timing Algorithm for Biopsy Device," issued May 10, 2011; U.S. Pat. No. 8,118,755, entitled "Biopsy Sample Storage," issued Feb. 21, 2012; U.S. Pub. No. 2008/0146962, entitled "Biopsy System with Vacuum Control Module," published Jun. 19, 2008; U.S. Pat. No. 8,251,916, entitled "Revolving Tissue Sample Holder for Biopsy Device," issued Aug. 28, 2012; and U.S. Pat. No. 8,532,747, entitled "Biopsy Marker Delivery Device," issued Sep. 10, 2013. The disclosure of each of the above-cited U.S. Patents and U.S. Patent Application Publications is incorporated by reference herein.

In some settings, it may be desirable to mark the location of a biopsy site for future reference. For instance, one or more markers may be deposited at a biopsy site before, during, or after a tissue sample is taken from the biopsy site. Exemplary marker deployment tools include the MAMMOMARK™, MICROMARK®, and CORMARK™ brand devices from Devicor Medical Products, Inc. of Cincinnati, Ohio. Further exemplary devices and methods for marking a biopsy site are disclosed in U.S. Pub. No. 2005/0228311, entitled "Marker Device and Method of Deploying a Cavity Marker Using a Surgical Biopsy Device," published Oct. 13, 2005, patented as U.S. Pat. No. 7,465,279; U.S. Pat. No. 6,996,433, entitled "Imageable Biopsy Site Marker," issued Feb. 7, 2006; U.S. Pat. No. 6,993,375, entitled "Tissue Site Markers for In Vivo Imaging," issued Jan. 31, 2006; U.S. Pat. No. 7,047,063, entitled "Tissue Site Markers for In Vivo Imaging," issued May 16, 2006; U.S. Pat. No. 7,229,417, entitled "Methods for Marking a Biopsy Site," issued Jun. 12, 2007; U.S. Pat. No. 7,044,957, entitled "Devices for Defining and Marking Tissue," issued May 16, 2006; U.S. Pat. No. 6,228,055, entitled "Devices for Marking and Defining Particular Locations in Body Tissue," issued May 8, 2001; and U.S. Pat. No. 6,371,904, entitled "Subcutaneous Cavity Marking Device and Method," issued Apr. 16, 2002. The disclosure of each of the above-cited U.S. Patents and U.S. Patent Application Publications is incorporated by reference herein.

While several systems and methods have been made and used for obtaining a biopsy sample, it is believed that no one prior to the inventor has made or used the invention described in the appended claims.

BRIEF DESCRIPTION OF THE DRAWINGS

While the specification concludes with claims which particularly point out and distinctly claim this technology, it is believed this technology will be better understood from the following description of certain examples taken in conjunction with the accompanying drawings, in which like reference numerals identify the same elements and in which:

Figure 1:
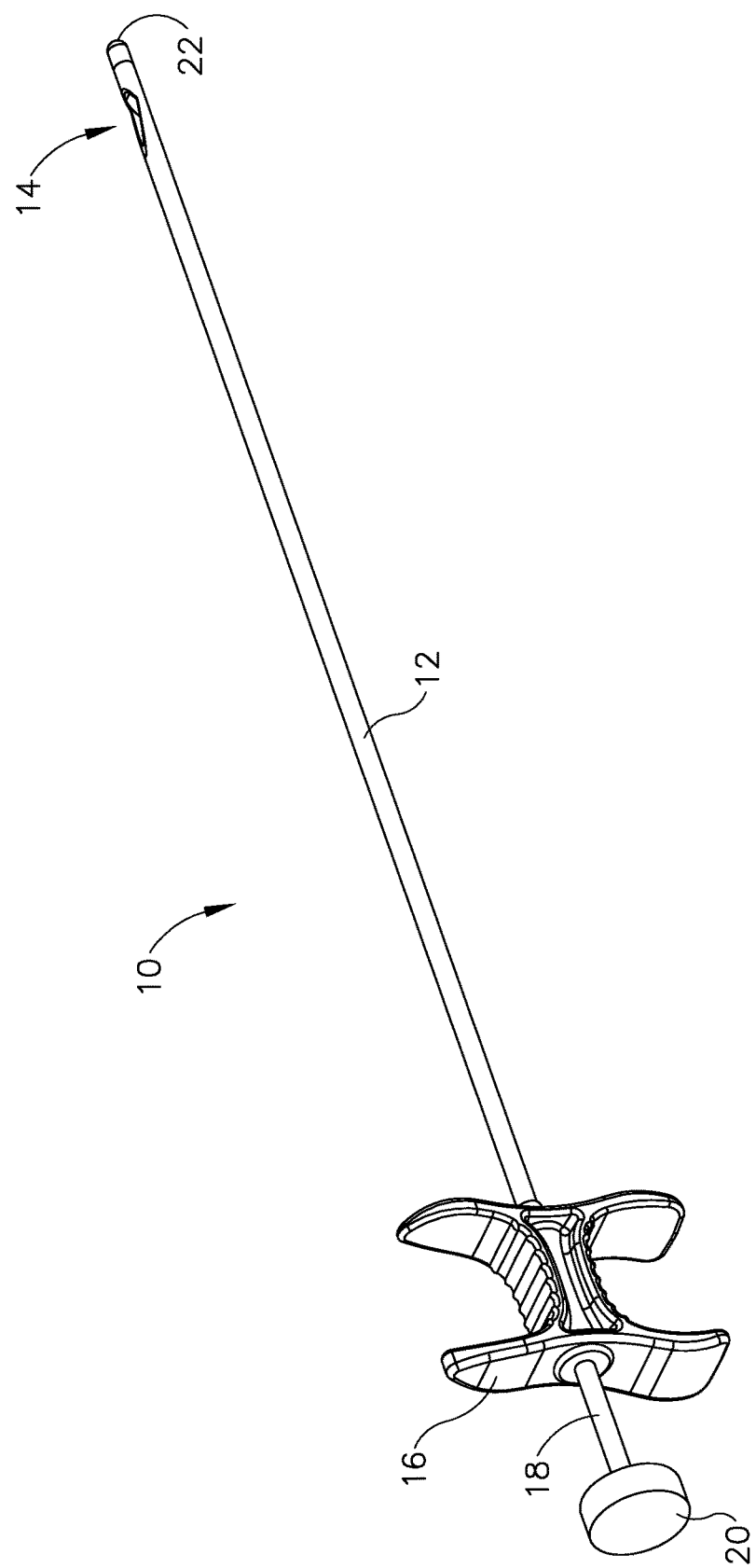
FIG. 1 depicts a perspective view of a marker delivery device.

The drawings are not intended to be limiting in any way, and it is contemplated that various embodiments of the technology may be carried out in a variety of other ways, including those not necessarily depicted in the drawings. The accompanying drawings incorporated in and forming a part of the specification illustrate several aspects of the present technology, and together with the description serve to explain the principles of the technology; it being understood, however, that this technology is not limited to the precise arrangements shown.

DETAILED DESCRIPTION

The following description of certain examples of the technology should not be used to limit its scope. Other examples, features, aspects, embodiments, and advantages of the technology will become apparent to those skilled in the art from the following description, which is by way of illustration, one of the best modes contemplated for carrying out the technology. As will be realized, the technology described herein is capable of other different and obvious aspects, all without departing from the technology. Accordingly, the drawings and descriptions should be regarded as illustrative in nature and not restrictive.

I. EXEMPLARY MARKER DELIVERY DEVICE

FIG. 1 illustrates a marker delivery device (10) which includes an elongate outer cannula (12) having a marker exit, such as side opening (14) formed adjacent to, but spaced proximally from, the distal end of the cannula (12).

A grip (16) can be provided at the proximal end of cannula (12). A push rod (18) can be provided, with push rod (18) extending coaxially in cannula (12) such that push rod (18) is configured to translate within cannula (12) to displace one or more markers through side opening (14) (see FIG. 2). Rod (18) may have sufficient rigidity in compression to push a marker from an internal lumen (15) of cannula (12) out through opening (14), yet be relatively flexible in bending. A plunger (20) is coupled at the proximal end of rod (18) for forcing rod (18) distally in cannula (12) to deploy a marker out of cannula (12).

A user may grasp grip (16) with two fingers, and may push on plunger (20) using the thumb on the same hand, so that marker delivery device (10) is operated by a user's single hand. A spring (not shown) or other feature may be provided about rod (18) to bias rod (18) proximally relative to grip (16) and cannula (12).

Figure 2:
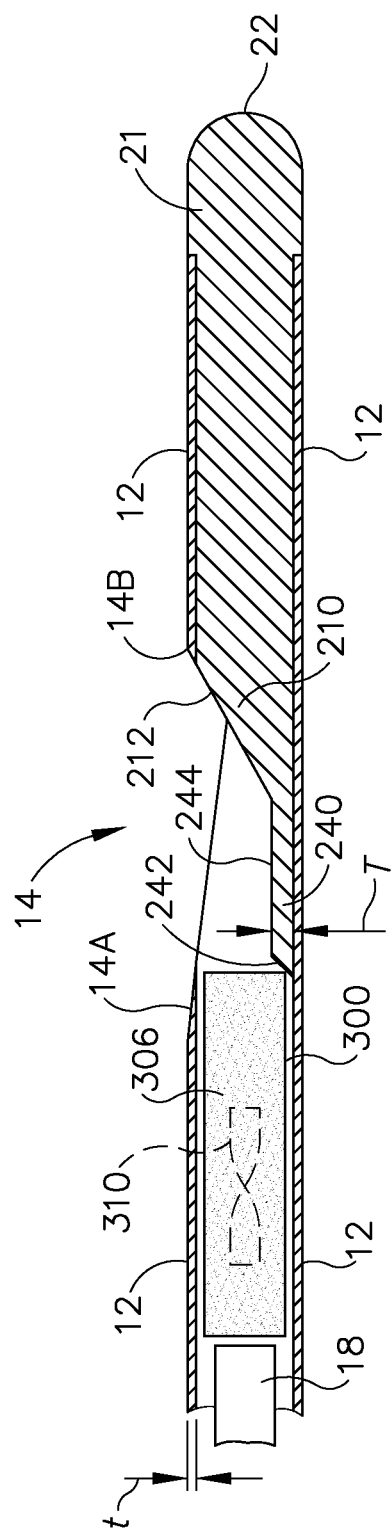
FIG. 2 depicts a cross-sectional view of a distal portion of the marker delivery device of FIG. 1.

FIG. 2 depicts a cross-sectional view of a distal portion of the marker delivery device (10). FIG. 2 shows a biopsy marker (300) disposed in internal lumen (15) of cannula (12). In the present example, marker (300) comprise a biodegradable or otherwise resorbable body (306), such as a generally cylindrically shaped body of collagen, and a metallic, generally radiopaque marker element (310) (shown in phantom) disposed within or otherwise carried by body (306).

Cannula (12) may be formed of any suitable metallic or non-metallic material. In some versions, cannula (12) is formed of a thin walled hollow tube formed of a suitable medical grade plastic or polymer. One suitable material is a thermoplastic elastomer, such as Polyether block amide (PEBA), such as is known under the tradename PEBAX. Cannula (12) may be formed of PEBAX, and may be substantially transparent to visible light and X-ray.

Side opening (14) may be formed by cutting away a portion of the wall of cannula (12). Side opening (14) communicates with an internal lumen (15) of cannula (12). Side opening (14) may extend axially (in a direction parallel to the axis of lumen (15)) from a proximal opening end (14A) to a distal opening end (14B), as illustrated in FIG. 2.

In the present example, distal tip (22) extends from the distal end of cannula (12) and is rounded as shown in FIG. 2. Referring to FIG. 2, the distal end of cannula (12) is closed by a unitary endpiece (21), with a portion of endpiece (21) extending into internal lumen (15) of cannula (12). Endpiece (21) may be a molded or cast component. Endpiece (21) comprises a tip (22), a ramp (210) having a ramp surface (212), and a marker engaging element (240). Ramp surface (212) aids in directing marker (300) from internal lumen (15) through side opening (14). Marker engaging element (240) helps to retain marker (300) in internal lumen (15) until the user intends to deploy marker (300).

Marker engaging element (240) is disposed within internal lumen (15), and at least a portion of marker engaging element (240) is disposed distally of proximal end (14A) of side opening (14). Marker engaging element (240) extends along a portion of the floor of cannula (12) under opening (14) such that marker engaging element (240) is positioned to reinforce the portion of cannula (12) in which opening (14) is formed. For instance, by positioning marker engaging element (240) underneath opening (14), as shown in FIG. 2, element (240) helps to stiffen cannula (12) in the region where wall of cannula (12) is cut to form opening (14). As shown in FIG. 2, marker engaging element (240) extends from the proximal most portion of ramp surface (212), and does not extend proximally of side opening (14), though in other embodiments, a portion of element (240) may extend proximally of opening (14).

As shown in FIG. 2, marker engaging element (240) is in the form of a step having a generally uniform thickness (T) along element's (240) axial length, except that element (240) has a tapered proximal end (242). Tapered proximal end (242) forms an included angle with the longitudinal axis of lumen (15) (included angle with a horizontal line in FIG. 2) of about 45 degrees, while ramp surface (212) forms an included angle with the longitudinal axis of about 30 degrees. Of course, any number of other suitable angles may be used. Thickness (T) may be greater than wall thickness (t) of cannula (12). In some versions, thickness (T) is at least about twice thickness (t). For instance, thickness (T) may be between about 0.018 inch to about 0.040 inch, and wall thickness (t) may be between about 0.005 inch to about 0.008 inch. The internal diameter of lumen (15) may be about 0.120 inches. Of course, any number of other suitable thicknesses and diameters may be used.

As shown in FIG. 2, an upwardly facing surface (244) (surface facing opening (14)) of marker engaging element (240) extends distally to contact ramp surface (212), so that there is not a space or gap between surface (244) and ramp surface (212). Such an arrangement is advantageous to reduce the possibility that marker (300), upon moving past marker engaging element (240), may become lodged between marker engagement element (240) and ramp (212). In some versions, marker engaging element (240), ramp (210), and/or tip (22) are formed of, or include, a material that is relatively more radiopaque than the wall of cannula (12). For instance, where element (240), ramp (210), and tip (22) are formed as an integral endpiece (21), endpiece (21) may include a radiopaque additive, such as barium sulfate. For instance, endpiece (21) may be a component molded of PEBAX, with about 20 percent by weight barium sulfate added to the molten PEBAX mold composition. The relatively more radiopaque marker engaging element (240), ramp (210), and tip (22) may be useful in distinguishing the position of those components using radiographic imaging. Also, where ramp (210) and/or step of engaging element (240) are positioned in association with opening (14), the addition of a radiopaque material can help identify the position of opening (14), and the position of marker (300) relative to opening (14) before, during, or after deployment of marker (300).

Only one marker (300) is shown disposed in lumen (15) in the figures. However, it should be understood that multiple markers (300) may be disposed in marker delivery device (10), such as in an end to end configuration. Markers (300) may have the same size and shape, or alternatively have different sizes and/or shapes.

Cannula (12) may be generally transparent to visible light and x-ray, and endpiece (21) may be generally opaque to visible light and x-ray. It may be desirable to color endpiece (21) with a dye or other suitable colorant in the liquid mold composition. For instance, it may be desirable to have different size markers (300) (e.g. length and/or diameter) for different biopsy procedures. For instance, it may be desirable to provide a larger marker (300) if a relatively large biopsy sample is taken, and a smaller marker (300) if a relatively small biopsy sample is taken. Endpiece (21) may be colored using one of multiple colors to indicate the size of marker (300) disposed in cannula (12). For instance, if three marker (300) sizes are provided, endpiece (21) may be colored one of three colors to identify which of marker (300) sizes are disposed in cannula (12) of a marker device (10). Endpiece (21) may also be colored to indicate a particular size (diameter or length) biopsy needle with which marker delivery device (10) is to be used. Additionally, multiple marker delivery devices (10) could be packaged in kit form, with the kit including marker delivery devices (10) having different size markers (300) and correspondingly colored endpieces (21).

Figure 3:
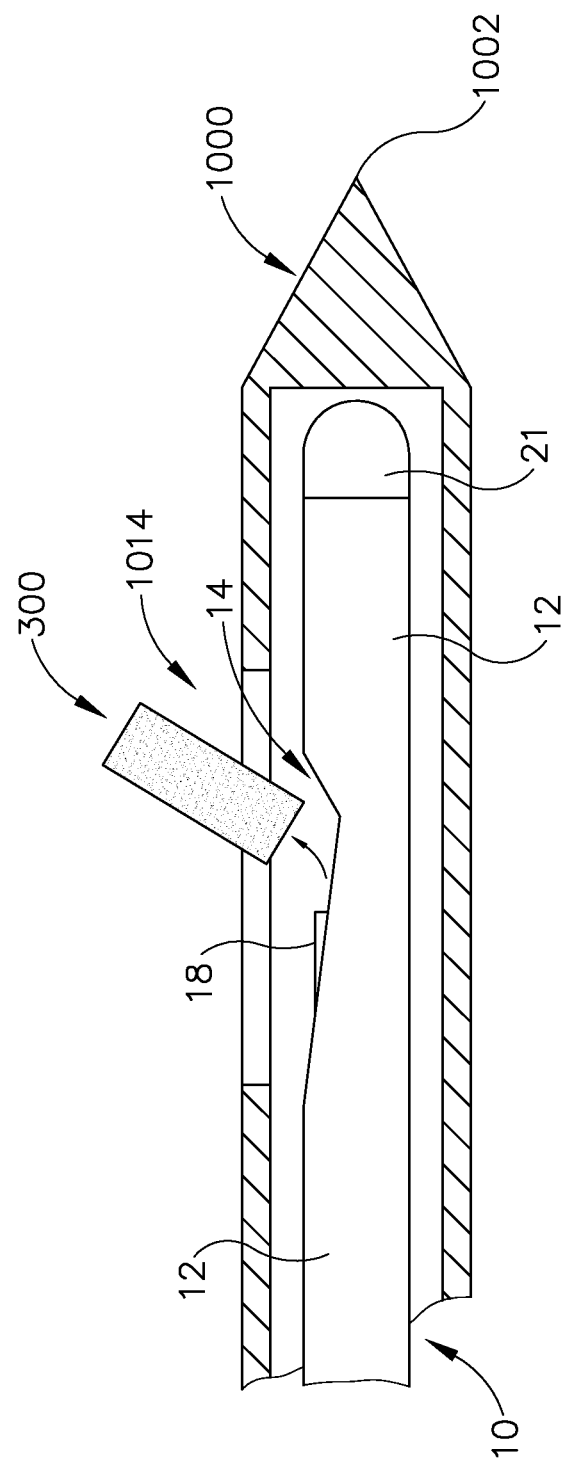
FIG. 3 depicts a cross-sectional view of a marker being deployed from the distal portion of the marker delivery device of FIG. 1 and through a lateral tissue receiving port in a biopsy needle to mark a biopsy site.

Referring to FIG. 3, marker delivery device (10) is used to deploy a marker (300) to mark a biopsy location within a patient. In FIG. 3, a cannular biopsy needle (1000) is shown having a closed distal end with piercing tip (1002) and a lateral tissue receiving aperture (1014). Marker deployer (10) is introduced to a biopsy site through biopsy needle (1000), which may be the same needle (1000) used to collect a tissue sample from the biopsy site. Biopsy needle (1000) may be of the type used with single insertion, multiple sample vacuum assisted biopsy devices. Several such biopsy devices are disclosed in the various patents and patent applications that have been referred to and incorporated by reference herein, though other biopsy devices may be used.

FIG. 3 shows the distal end of marker deployer (10) disposed within needle (1000). Needle (1000) may be positioned in tissue, and a biopsy sample may be obtained through opening (1014), thereby providing a biopsy cavity adjacent opening (1014). Then, after the tissue sample has been obtained and transferred proximally through needle (1000), and without removing needle (1000) from the patient's tissue, deployer (10) is inserted into a proximal opening in needle (1000). In FIG. 3, needle (1000) and deployer (10) are positioned such that opening (14) of cannula (12) and opening (1014) of needle (1000) are substantially aligned axially and circumferentially. Then, with deployer (10) and needle (1000) so positioned at the biopsy site, push rod (18) is advanced to deploy marker (300) up ramp surface (212), through opening (14), and then through opening (1014), into the biopsy cavity.

In some instances, distal opening end (14B) may not align with ramped surface (212) due to inadvertent errors during manufacturing and/or assembly of marker delivery device (10). Accordingly, a marker (300) may become caught on distal opening end (14B) when marker (300) is deployed from device (10). It may therefore be desirable to include a second ramped feature on endpiece (21) to allow smooth deployment of marker (300) from device (10) even if ramped surface (212) and distal opening end (14B) are misaligned, as will be seen below.

Figure 4:
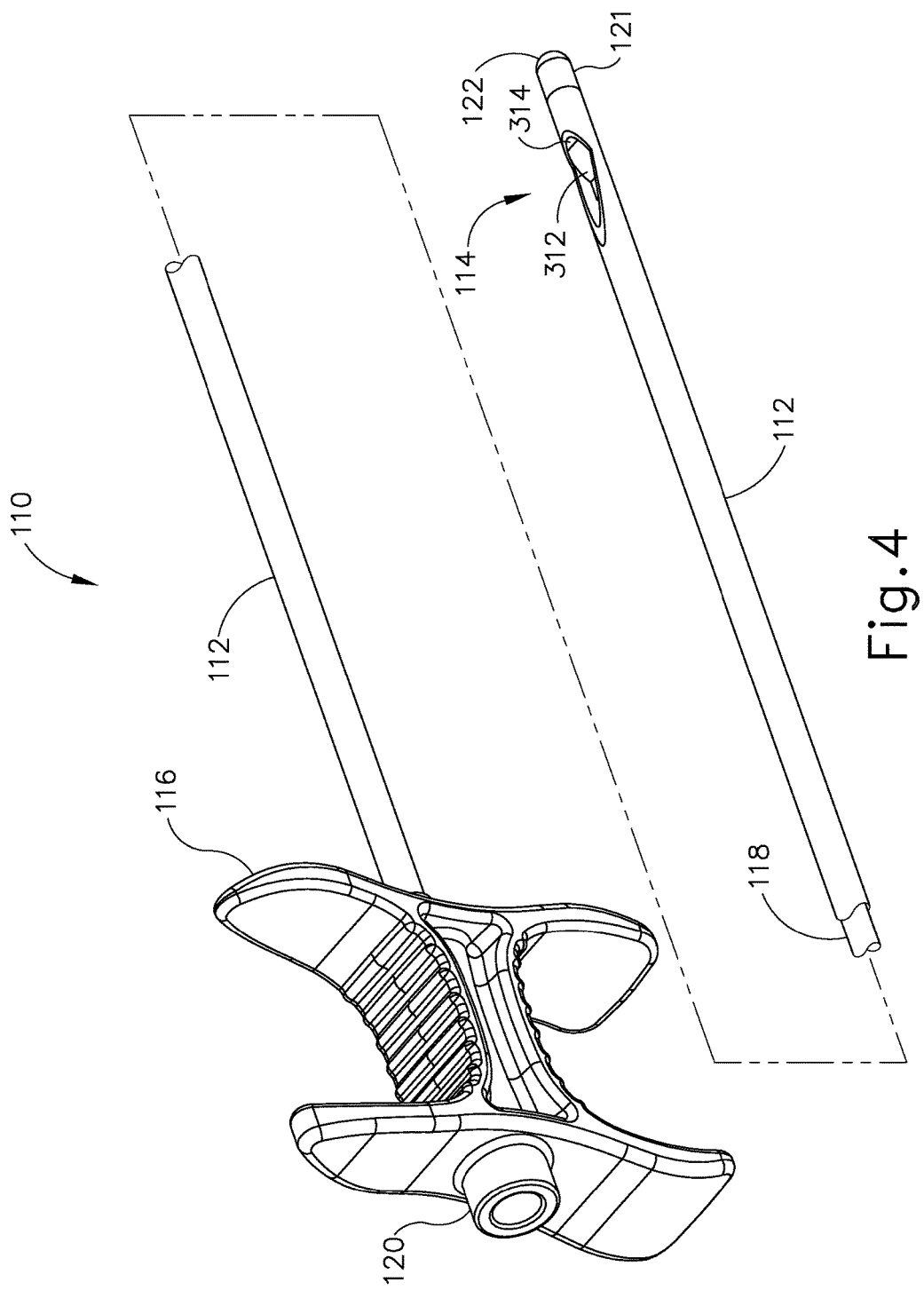
FIG. 4 depicts a perspective view of another exemplary marker delivery device.
Figure 5:
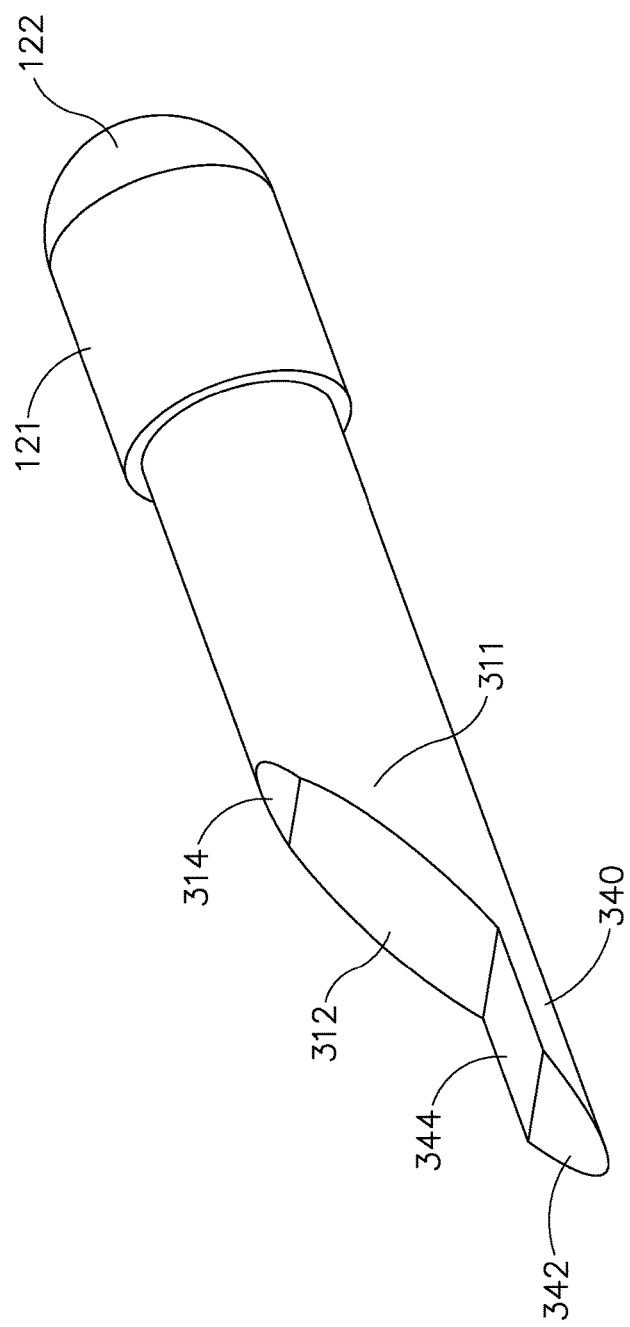
FIG. 5 depicts a perspective view of an endpiece of the marker delivery device of FIG. 4.

FIG. 4 shows another exemplary marker delivery device (110) that is similar to marker delivery device (10), except that marker delivery device (110) comprises a compound ramped endpiece (121). Like marker deliver device (10), marker delivery device (110) comprises a cannula (112), a side opening (114), a grip (116), a plunger (120), and an endpiece (121). As shown in FIG. 5, endpiece (121) is similar to endpiece (21) in that endpiece (121) comprises a ramp (311), and a rounded distal tip (122). Marker engaging element (340) and tip (122) are similar to tip (22). Ramp (311) is similar to ramp (210), except that ramp (311) comprises a first ramped surface (312) and a second ramped surface (314) distal to first ramped surface (312). Second ramped surface (314) inclines at a smaller angle than first ramped surface (312) relative to the longitudinal axis of endpiece (121).

Figure 6:
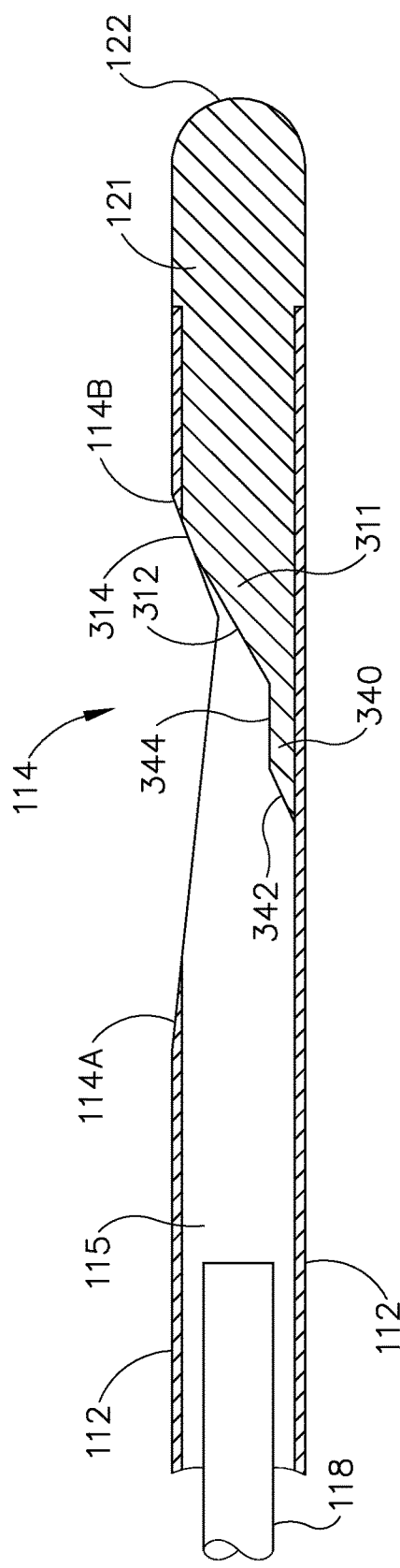
FIG. 6 depicts a cross-sectional view of a distal portion of the marker delivery device of FIG. 4.

FIG. 6 shows endpiece (121) coupled with cannula (112), such that a portion of endpiece (121) is inserted within a distal portion of cannula (112). Marker engaging element (340) is adjacent to side opening (114) of cannula (112). A tapered proximal end (342) of marker engaging element (340) forms an included angle with the longitudinal axis of lumen (115) of about 45 degrees. First ramped surface (312) forms an included angle with the longitudinal axis of lumen (115) of about 30 degrees. Second ramped surface (314) forms an included angle with the longitudinal axis of lumen (115) of about 21 degrees. Of course, any number of other suitable angles may be used. A distal opening end (114B) of opening (114) is formed at substantially the same angle as second ramped surface (314) such that second ramped surface (314) and distal opening end (114B) of cannula (112) form a substantially flush surface when endpiece (121) is inserted within cannula (112). For instance, endpiece (121) may be insert molded within cannula (112) and formed with tapered proximal end (342), marker engagement element (340), and first ramped surface (312). Side opening (114) may then be cut to form a proximal opening end (114A), distal opening end (114B), and second ramped surface (314) of endpiece (121). This creates a substantially flush surface between cannula (112) and endpiece (121). In some other versions, endpiece (121) may be manufactured and then assembled with cannula (112). Second ramped surface (314) and distal opening end (114B) may then be cut together after assembly of endpiece (121) and cannula (112). In some other versions, second ramped surface (314) and distal opening end (114B) may be cut and then assembled together. Even if second ramped surface (314) and distal opening end (114B) are inadvertently misaligned during assembly, a marker (300) may smoothly deploy from device (110) because second ramped surface (314) and distal opening end (114B) have a shallower angle than first ramped surface (312).

Marker delivery device (110) may be used to deploy a marker (300) to mark a biopsy location within a patient. For instance, marker delivery device (110) may introduced to a biopsy site through a biopsy needle (1000), which may be the same needle (1000) used to collect a tissue sample from the biopsy site. Needle (1000) may be positioned in tissue, and a biopsy sample may be obtained through opening (1014), thereby providing a biopsy cavity adjacent opening (1014). Then, after the tissue sample has been obtained and transferred proximally through needle (1000), and without removing needle (1000) from the patient's tissue, marker delivery device (110) is inserted into a proximal opening in needle (1000). Needle (1000) and marker delivery device (110) are positioned such that opening (114) of cannula (112) and opening (1014) of needle (1000) are substantially aligned axially and circumferentially. A marker (300) is positioned within lumen (115) of cannula (112) proximal to marker engaging element (340) such that marker engaging element (340) holds marker (300) within cannula (112). Then, with deployer (110) and needle (1000) so positioned at the biopsy site, a push rod (118) is advanced to deploy marker (300). As push rod (118) advances marker (300), marker (300) cammingly slides along ramped proximal end (342) of marker engaging element (340), along an upwardly facing surface (344) and up first and second ramped surface (312, 314). Marker (300) is then deployed through opening (114), and then through opening (1014) of needle (1000), into the biopsy cavity.

II. EXEMPLARY MARKER

Figure 7:
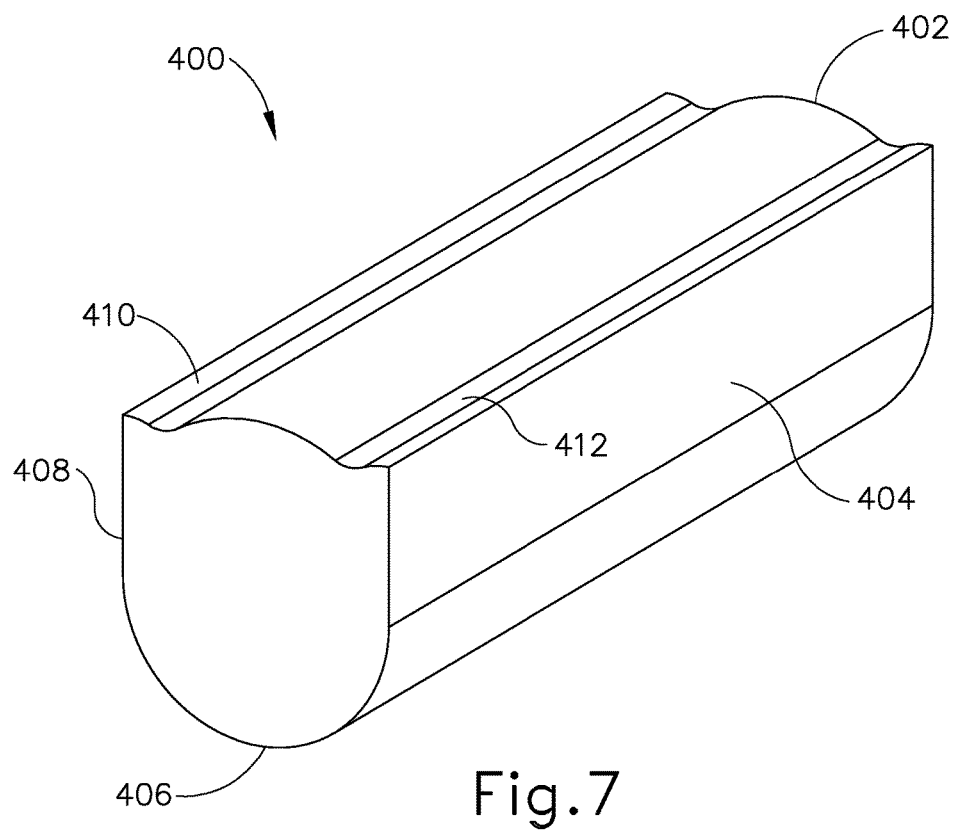
FIG. 7 depicts a perspective view of an exemplary marker for use with the marker delivery device of FIG. 4.
Figure 8:
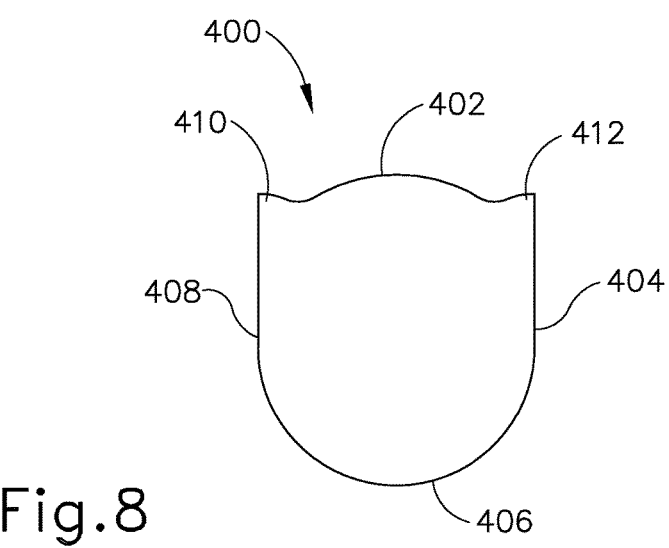
FIG. 8 depicts a front view of the marker of FIG. 7.

FIGS. 7-8 show an exemplary marker (400) that may be deployed from a marker delivery device (10, 110) to mark a biopsy site. Marker (400) is similar to marker (300) described above, except that marker (400) has a modified shape compared to the cylindrical shape of marker (300). As best seen in FIG. 8, marker (400) comprises a rounded top surface (402) positioned between corners (410, 412) extending outwardly from marker (400). A side surface (408) extends downwardly from corner (410) and an opposing side surface (404) extends downwardly from corner (412). A rounded bottom surface (406) joins side surfaces (404, 408). Marker (400) is biodegradable or otherwise resorbable. Accordingly, marker (400) may be made of collagen or any other suitable material, including but not limited to the various marker body materials taught in the various references cited herein. Marker (400) comprises a generally radiopaque (e.g., metallic) marker element (not shown) disposed within or otherwise carried by marker (400).

Figure 9:
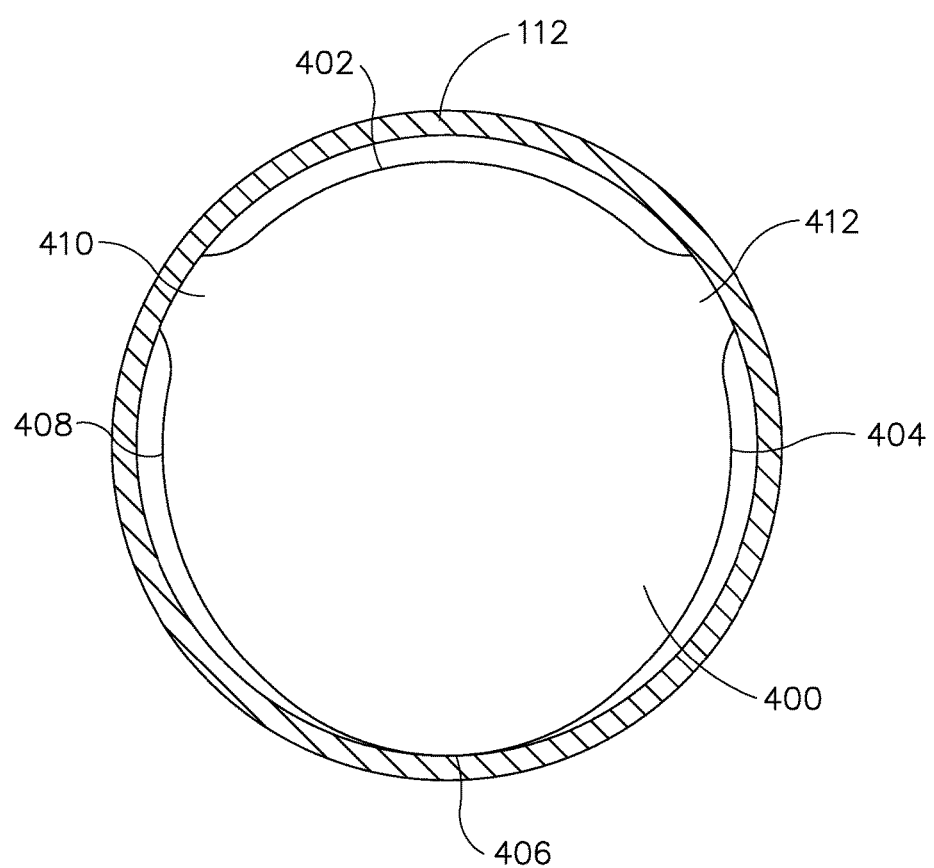
FIG. 9 depicts a cross-sectional view of the marker of FIG. 7 within a shaft of the marker delivery device of FIG. 4.

Marker (400) may be inserted within cannula (12, 112) of a marker delivery device (10, 110) for deployment to a biopsy site, as shown in FIG. 9. When marker (400) is inserted within cannula (12, 112), corners (410, 412) and bottom surface (406) engage the inner diameter of cannula (12, 112). Accordingly, corners (410, 412) may flex inwardly or otherwise deform when corners (410, 412) engage cannula (12, 112). This may cause side surfaces (404, 408) to deflect outwardly. In some versions, side surfaces (404, 408) deflect outwardly to contact the inner diameter of cannula (12, 112), while in other versions, side surfaces fail to contact the inner diameter of cannula (12, 112). The contact of corners (410, 412) and bottom surface (406) of marker (400) with cannula (12, 112) provides sufficient frictional resistance between marker (400) and cannula (12, 112) to prevent marker (400) from inadvertently falling out of side opening (14, 114) before push rod (18, 118) is actuated to deploy marker (400), while still allowing marker (400) to be deployed from cannula (12, 112) without requiring excessive force. Because marker (400) engages cannula (12, 112) with corners (410, 412), the force needed to push marker (400) out of cannula (12, 112) may be less than the force needed to push marker (300) out of cannula (12, 112).

Figure 10:
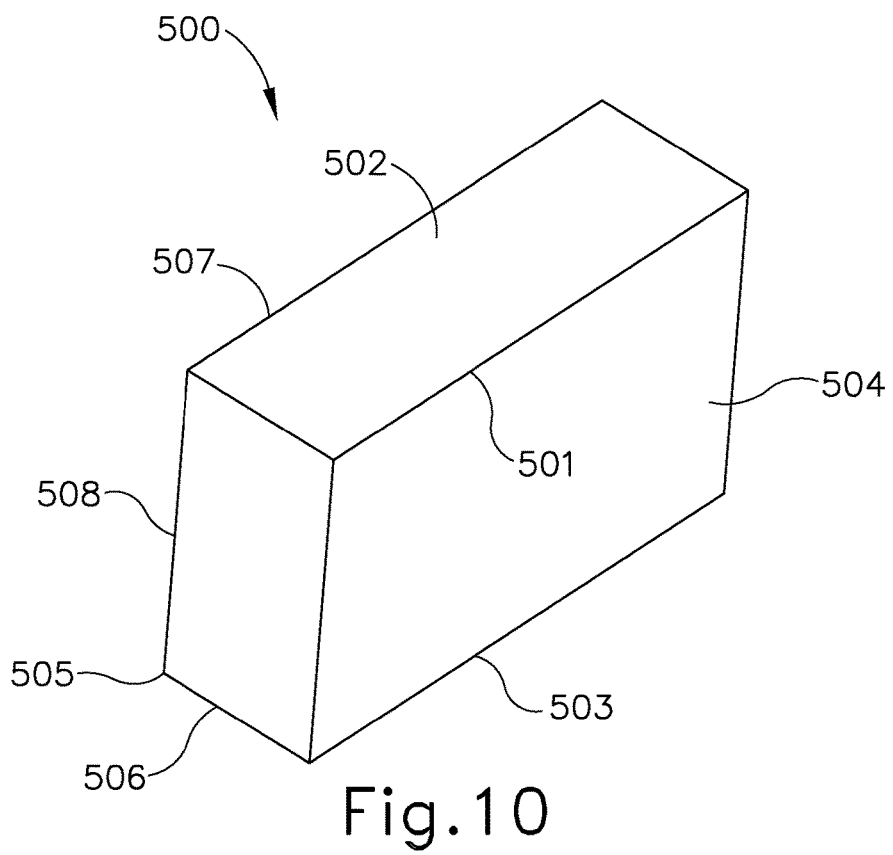
FIG. 10 depicts a perspective view of another exemplary marker for use with the marker delivery device of FIG. 4.
Figure 11:
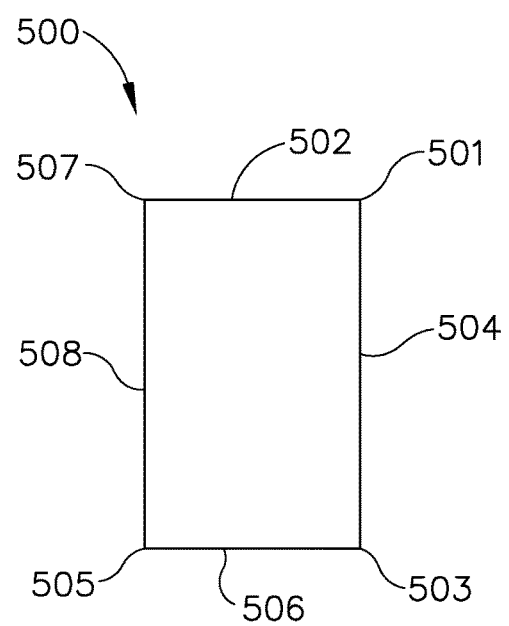
FIG. 11 depicts a front view of the marker of FIG. 10.

FIGS. 10-11 show another exemplary marker (500) that may be deployed from a marker delivery device (10, 110) to mark a biopsy site. Marker (500) is similar to marker (300) described above, except that marker (500) has a modified shape compared to the cylindrical shape of marker (300). As best seen in FIG. 11, marker (500) comprises a rectangular shape having a top surface (502), a bottom surface (506), and side surfaces (504, 508). Accordingly, surfaces (502, 504, 506, 508) form corners (501, 503, 505, 507) between surfaces (502, 504, 506, 508). Although marker (500) has a rectangular shape in the present example, marker (500) may also comprise other suitable shapes, such as a square, triangle, pentagon, or other polygons. Marker (500) is biodegradable or otherwise resorbable. Accordingly, marker (500) may be made of collagen or any other suitable material, including but not limited to the various marker body materials taught in the various references cited herein. Marker (500) comprises a generally radiopaque (e.g., metallic) marker element (not shown) disposed within or otherwise carried by marker (500).

Figure 12:
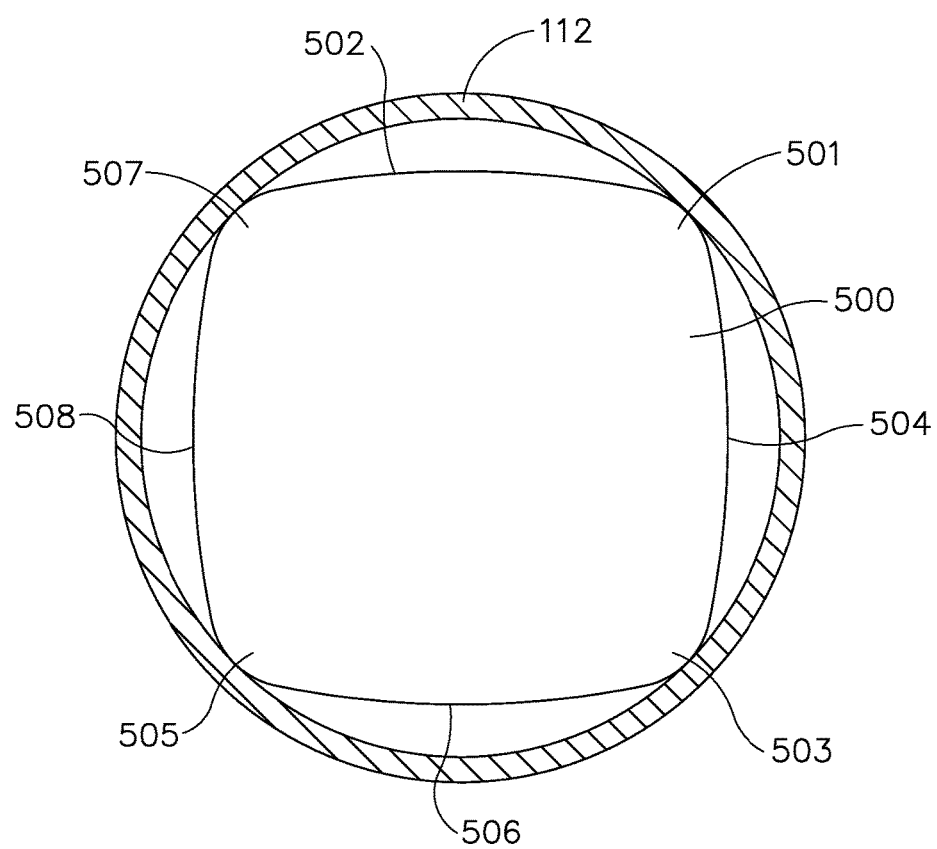
FIG. 12 depicts a cross-sectional view of the marker of FIG. 10 within a shaft of the marker delivery device of FIG. 4.

Marker (500) may be inserted within cannula (12, 112) of a marker delivery device (10, 110) for deployment to a biopsy site, as shown in FIG. 12. When marker (500) is inserted within cannula (12, 112), corners (501, 503, 505, 507) engage the inner diameter of cannula (12, 112). Accordingly, corners (501, 503, 505, 507) may flex inwardly or otherwise deform when corners (501, 503, 505, 507) engage cannula (12, 112). This may cause surfaces (502, 504, 506, 508) to deflect outwardly. In some versions, surfaces (502, 504, 506, 508) deflect outwardly to contact the inner diameter of cannula (12, 112), while in other versions, surfaces (502, 504, 506, 508) fail to contact the inner diameter of cannula (12, 112). The contact of corners (501, 503, 505, 507) of marker (500) with cannula (12, 112) provides sufficient frictional resistance between marker (500) and cannula (12, 112) to prevent marker (500) from inadvertently falling out of side opening (14, 114) before push rod (18, 118) is actuated to deploy marker (500), while still allowing marker (500) to be deployed from cannula (12, 112) without requiring excessive force. Because marker (500) engages cannula (12, 112) with corners (501, 503, 505, 507), the force needed to push marker (500) out of cannula (12, 112) may be less than the force needed to push marker (300) out of cannula (12, 112).

Figure 13:
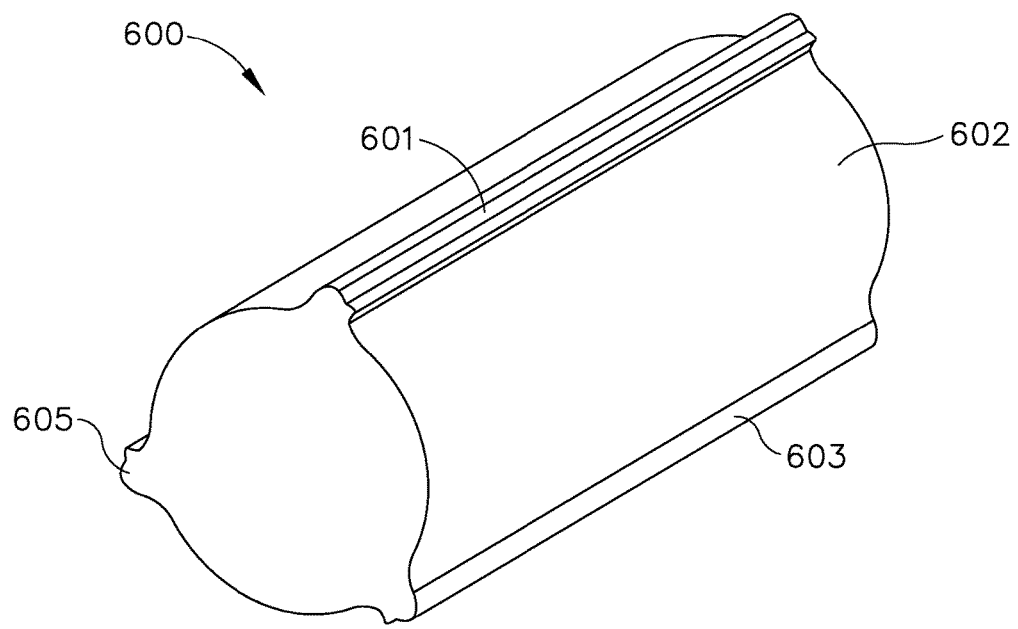
FIG. 13 depicts a perspective view of another exemplary marker for use with the marker delivery device of FIG. 4.
Figure 14:
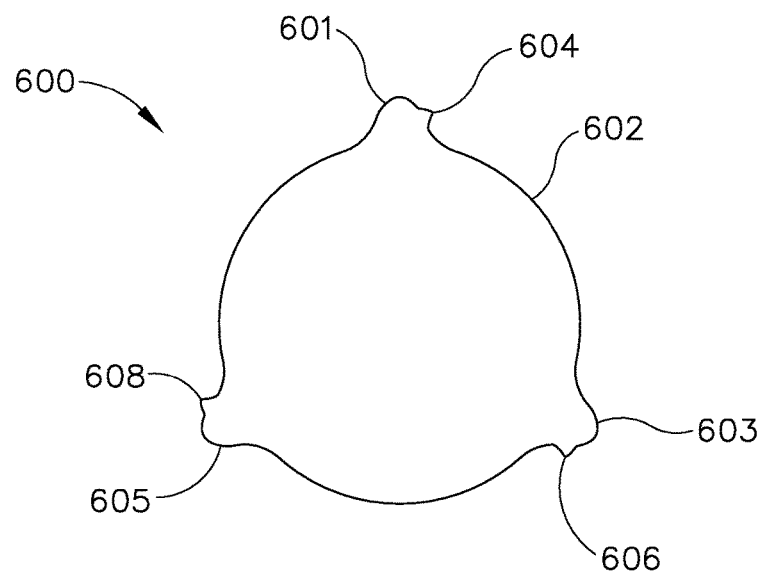
FIG. 14 depicts a front view of the marker of FIG. 13.

FIGS. 13-14 show another exemplary marker (600) that may be deployed from a marker delivery device (10, 110) to mark a biopsy site. Marker (600) is similar to marker (300) described above, except that marker (600) comprises a plurality of ribs (601, 603, 605) extending outwardly from marker (600). Ribs (601, 603, 605) extend longitudinally along exterior surface (602) of marker (600) and are equally spaced around exterior surface (602) of marker (600). Although three ribs (601, 603, 605) are shown, any other suitable number of ribs (601, 603, 605) may be used. Ribs (601, 603, 605) may also be unevenly positioned around exterior surface (602) of marker (600). As best seen in FIG. 14, each rib (601, 603, 605) comprises a protrusion (604, 606, 608) extending outwardly from each rib (601, 603, 605). The diameter of marker (600) may be about 0.066 inches. Ribs (601, 603, 605) may extend beyond the diameter of marker (600) by about 0.0025 inches. Of course any other suitable diameters and lengths may be used. It should be noted that protrusions (604, 606, 608) are merely optional. Marker (600) is biodegradable or otherwise resorbable. Accordingly, marker (600) may be made of collagen or any other suitable material, including but not limited to the various marker body materials taught in the various references cited herein. Marker (600) comprises a generally radiopaque (e.g., metallic) marker element (not shown) disposed within or otherwise carried by marker (600).

Figure 15:
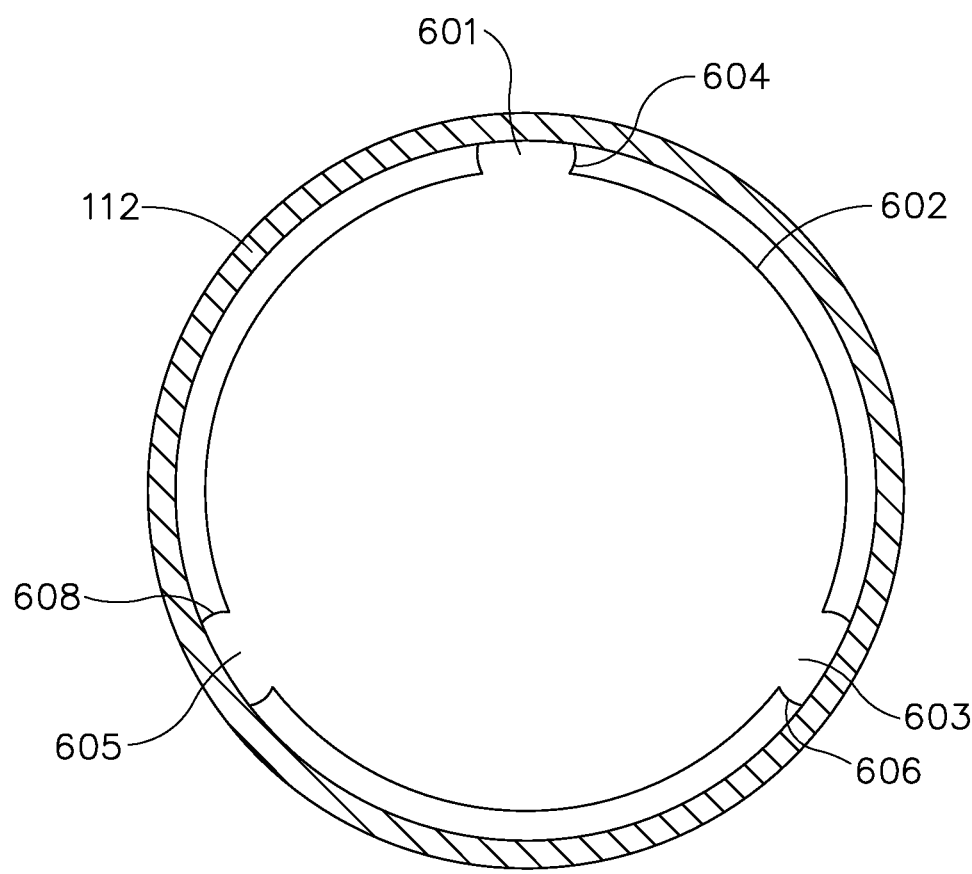
FIG. 15 depicts a cross-sectional view of the marker of FIG. 13 within a shaft of the marker delivery device of FIG. 4.

Marker (600) may be inserted within cannula (12, 112) of a marker delivery device (10, 110) for deployment to a biopsy site, as shown in FIG. 15. When marker (600) is inserted within cannula (12, 112), ribs (601, 603, 605) engage the inner diameter of cannula (12, 112). Accordingly, ribs (601, 603, 605) may flex inwardly or otherwise deform when ribs (601, 603, 605) engage cannula (12, 112). Ribs (601, 603, 605) may deflect such that protrusions (604, 606, 608) engage the inner diameter of cannula (12, 112). Accordingly, protrusions (604, 606, 608) may help to maintain marker (600) within cannula (12, 112). Exterior surface (602) of marker (600) may also deflect outwardly when marker (600) is inserted within cannula (12, 112). In some versions, surface (602) deflects outwardly to contact the inner diameter of cannula (12, 112), while in other versions, surface (602) fails to contact the inner diameter of cannula (12, 112). The contact of ribs (601, 603, 605) and/or protrusions (604, 606, 608) of marker (600) with cannula (12, 112) provides sufficient frictional resistance between marker (600) and cannula (12, 112) to prevent marker (600) from inadvertently falling out of side opening (14, 114) before push rod (18, 118) is actuated to deploy marker (600), while still allowing marker (600) to be deployed from cannula (12, 112) without requiring excessive force. Because marker (600) engages cannula (12, 112) with ribs (601, 603, 605), the force needed to push marker (600) out of cannula (12, 112) may be less than the force needed to push marker (300) out of cannula (12, 112).

III. CONCLUSION

It should be appreciated that any patent, publication, or other disclosure material, in whole or in part, that is said to be incorporated by reference herein is incorporated herein only to the extent that the incorporated material does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

Embodiments of the present invention have application in conventional endoscopic and open surgical instrumentation as well as application in robotic-assisted surgery.

By way of example only, embodiments described herein may be processed before surgery. First, a new or used instrument may be obtained and if necessary cleaned. The instrument may then be sterilized. In one sterilization technique, the instrument is placed in a closed and sealed container, such as a plastic or TYVEK bag. The container and instrument may then be placed in a field of radiation that can penetrate the container, such as gamma radiation, x-rays, or high-energy electrons. The radiation may kill bacteria on the instrument and in the container. The sterilized instrument may then be stored in the sterile container. The sealed container may keep the instrument sterile until it is opened in a medical facility. A device may also be sterilized using any other technique known in the art, including but not limited to beta or gamma radiation, ethylene oxide, or steam.

Embodiments of the devices disclosed herein can be reconditioned for reuse after at least one use. Reconditioning may include any combination of the steps of disassembly of the device, followed by cleaning or replacement of particular pieces, and subsequent reassembly. In particular, embodiments of the devices disclosed herein may be disassembled, and any number of the particular pieces or parts of the devices may be selectively replaced or removed in any combination. Upon cleaning and/or replacement of particular parts, embodiments of the devices may be reassembled for subsequent use either at a reconditioning facility, or by a surgical team immediately prior to a surgical procedure. Those skilled in the art will appreciate that reconditioning of a device may utilize a variety of techniques for disassembly, cleaning/replacement, and reassembly. Use of such techniques, and the resulting reconditioned device, are all within the scope of the present application.

Having shown and described various embodiments of the present invention, further adaptations of the methods and systems described herein may be accomplished by appropriate modifications by one of ordinary skill in the art without departing from the scope of the present invention. Several of such potential modifications have been mentioned, and others will be apparent to those skilled in the art. For instance, the examples, embodiments, geometrics, materials, dimensions, ratios, steps, and the like discussed above are illustrative and are not required. Accordingly, the scope of the present invention should be considered in terms of the following claims and is understood not to be limited to the details of structure and operation shown and described in the specification and drawings.

We claim:
1. A marker delivery device comprising:
  (a) a marker deployer cannula including:
    (i) a distal end;
    (ii) a proximal end;
    (iii) an internal lumen; and
    (iv) a side opening including a distal side opening end; the side opening being spaced proximal to the distal end of the marker deployer cannula, and the side opening being in communication with the internal lumen;
  (b) a push rod, the push rod being slidably disposed within the marker deployer cannula;
  (c) a biopsy site marker; and
  (d) an endpiece, the endpiece including:
    (i) a distal tip; and
    (ii) a ramp having a first ramped surface and a second ramped surface, the ramp extending proximally from the distal tip, the first ramped surface being positioned proximally to, and directly adjacent to, the second ramped surface, the first ramped surface having a first incident angle, the second ramped surface having a second incident angle, the first incident angle differing from the second incident angle, the second ramped surface being configured to align with the distal side opening end; and
  (e) a marker engaging step extending from the ramp, the marker engaging step including a proximal end configured to selectably hold the biopsy site marker within the marker deployer cannula;
  the endpiece being insertable into the distal end of the marker deployer cannula;
  the marker delivery device being operable to deploy the biopsy site marker at a biopsy site; and
  the first incident angle of the first ramped surface being larger than the second incident angle of the second ramped surface.

2. The marker delivery device of claim 1, the marker engaging step extending proximally from the ramp.

3. The marker delivery device of claim 1, the proximal end of the marker engaging step including a tapered proximal end.

4. The marker delivery device of claim 1, the distal side opening end including a third incident angle.

5. The marker delivery device of claim 1, the distal side opening end having a third incident angle that is substantially the same as the second incident angle of the second ramped surface of the endpiece.

6. The marker delivery device of claim 1, the biopsy site marker including outwardly extending edges, the outwardly extending edges including a plurality of ribs extending from a substantially cylindrical surface of the biopsy site marker.

7. The marker delivery device of claim 6, each rib of the plurality of ribs including a protrusion, each protrusion being configured to engage at least a portion of the internal lumen of the marker deployer cannula.

8. The marker delivery device of claim 1, the biopsy site marker including outwardly extending edges, the outwardly extending edges being defined by four sides of the biopsy site marker.

9. The marker delivery device of claim 8, each side of the four sides being joined to another side to form each outwardly extending edge of the plurality of edges of the biopsy site marker.

10. The marker delivery device of claim 1, the biopsy site marker further including a rounded bottom surface, the bottom surface being configured to engage at least a portion of the internal lumen of the marker deployer cannula.

11. The marker delivery device of claim 10, the biopsy site marker including a plurality of outwardly extending edges, the plurality of outwardly extending edges including two corners, the two corners being defined by two side surfaces extending from the rounded bottom surface and a rounded top surface.

12. A system comprising:
(a) a biopsy device including a biopsy needle, the biopsy needle having a distal end including a tissue piercing tip, and a tissue receiving aperture placed proximally to the distal end;
(b) a marker delivery device including:
(i) a marker deployer cannula having an inner surface and including a distal end, an internal lumen, and a marker exit, the marker exit being spaced proximal to the distal end of the marker deployer cannula, the marker exit being in communication with the internal lumen, and the marker exit including a marker exit distal end;
(ii) a push rod, the push rod being slidably disposed in the marker deployer cannula, and
(iii) an endpiece including:
(1) a distal tip,
(2) a ramp having a first ramped surface at a first incident angle and a second ramped surface at a second incident angle, the first ramped surface being positioned proximally to, and directly adjacent to, the second ramped surface, the first incident angle being greater than the second incident angle, and
(3) a marker stop extending from the ramp; and
(c) a biopsy site marker, the biopsy site marker having a plurality of edges and a plurality of surfaces, each edge of the plurality of edges being configured to engage at least a portion of an inner diameter of the marker deployer cannula, and each surface of the plurality of surfaces being configured to deflect outwardly toward the inner surface of the cannula, the marker stop having an end portion, the end portion being configured to releasably hold the biopsy site marker within the marker deployer cannula;
the marker delivery device being configured to be insertable into the biopsy device such that the marker exit of the marker delivery device is aligned with the tissue receiving aperture of the biopsy device, the push rod being configured to urge the biopsy site marker up the ramp of the endpiece and through the tissue receiving aperture of the biopsy device.

13. The system of claim 12, each edge of the plurality of edges of the biopsy site marker including a rib, the rib including at least one protrusion, the rib and the protrusion of each edge of the plurality of edges being configured to engage at least a portion of the inner diameter of the marker deployer cannula.

14. The system of claim 12, the biopsy site marker including a top rounded surface and a rounded bottom surface, the rounded bottom surface defining two side surfaces, the side surfaces and the rounded top surface together defining a first edge and a second edge of the plurality of edges.

15. The system of claim 12, the biopsy site marker including compressed-collagen.

16. A marker delivery device comprising:
(a) a cannula including a proximal end, a distal tip, a side opening, and a grip coupled to the cannula, the side opening being positioned toward the proximal end of the cannula relative to the distal tip, the side opening including a distal end;
(b) at least one biopsy marker disposed proximally to the side opening of the cannula;
(c) a push rod, having a plunger coupled to the push rod, the push rod being slidably disposed within the cannula so as to extend proximal to the at least one biopsy marker; and
(d) an endpiece disposed within the distal end of the cannula, the endpiece including a distal tip a compound ramp, and a marker engagement element, at least a portion of the distal tip extending distally from the distal end of the cannula, the compound ramp extending proximally from the distal end of the endpiece, the compound ramp including a first ramped surface having a first incident angle, the first ramped surface being adjacent to a second ramped surface, the second ramped surface having a second incident angle that differs from the first incident angle in that the first incident angle is greater than the second incident angle, the second ramped surface being configured to align with the distal end of the side opening, the marker engagement element including a proximal end portion, the proximal end portion being configured to releasably secure the at least one biopsy marker within the cannula relative to the side opening;
the grip and the plunger being configured to be manipulated by a single hand, the push rod being movable in a distal direction to deploy the at least one biopsy marker from the cannula through the side opening.

17. A marker delivery device comprising:
(a) a marker deployer cannula including:
(i) a distal end;
(ii) a proximal end;
(iii) an internal lumen; and
(iv) a marker exit including a marker exit distal end, the marker exit distal end including an angled surface; the marker exit being spaced proximal to the distal end of the marker deployer cannula, and the marker exit being in communication with the internal lumen;
(b) a push rod, the push rod being slidably disposed within the marker deployer cannula;
(c) a biopsy site marker; and
(d) an endpiece including:
(i) a distal tip; and
(ii) an inclined portion having a first ramped surface at a first incident angle and a second ramped surface at a second incident angle less than the first incident angle, the inclined portion extending proximally from the distal tip, and the first ramped surface is positioned proximally to, and directly adjacent to, the second ramped surface, the second ramped surface being configured to align with the angled surface of the marker exit distal end; the endpiece being insertable into the distal end of the marker deployer cannula; and the marker delivery device being operable to deploy the biopsy site marker at a biopsy site; and (iii) a marker engaging step extending from the inclined portion, the marker engaging step having a proximal end configured to releasably engage the biopsy site marker.

\* \* \* \* \*